United States Patent [19]
Weaver et al.

[11]    4,413,289
[45]    Nov. 1, 1983

[54] DIGITAL RECORDING AND PLAYBACK METHOD AND APPARATUS

[75] Inventors: Charles S. Weaver, Palo Alto; Joseph H. Chadwick, Menlo Park, both of Calif.

[73] Assignee: SRI International, Menlo Park, Calif.

[21] Appl. No.: 243,593

[22] Filed: Mar. 13, 1981

[51] Int. Cl.³ ............................ G11B 5/09; G11B 5/00
[52] U.S. Cl. ............................................. 360/51; 360/8
[58] Field of Search ................................ 360/8, 32, 51

[56] References Cited

U.S. PATENT DOCUMENTS

| 3,571,801 | 3/1971 | Coolidge et al. | 360/51 |
|---|---|---|---|
| 3,803,632 | 4/1974 | Irwin et al. | 360/51 |
| 3,838,445 | 9/1974 | Cupp et al. | 360/32 |
| 3,975,761 | 8/1976 | Taudt et al. | 360/32 |
| 4,143,407 | 3/1979 | Liberry | 360/51 |
| 4,224,642 | 9/1980 | Mawatari et al. | 360/32 |

OTHER PUBLICATIONS

"Compression of the ECG by Prediction or Interpolation and Entropy Encoding"–U. E. Ruttimann et al., IEEE Transactions, vol. BMG-26, #11, 11/79.
"A Computer System for Capturing Transient Electrocardiagraphic Data"–K. L. Ripley et al., Proc. Comput. Cardiol., pp. 439-445, 1976.

Primary Examiner—Vincent P. Canney
Attorney, Agent, or Firm—Victor R. Beckman

[57]    ABSTRACT

A recording-playback system is disclosed wherein analog signals are converted to digital form which then are compressed and encoded using a variable length code. The encoded signals are temporarily stored in a buffer memory from which they are read out to a variable speed recorder for recording thereof. The rate at which the encoded signals are read out to the recorder and the recording speed are controlled in direct proportion to the percent fullness of the buffer memory for recording with substantially constant bit density on the recording medium. The ratio of the buffer memory read out rate and recording speed may be selected for recording with a substantially maximum bit density. A playback unit for the system includes a variable speed playback for playing back the recorded digital signals. The signals are temporarily stored in a buffer memory, from which memory they are read out to a decoder which operates at a substantially constant word rate. The speed of operation of the variable speed playback means is controlled in inverse proportion to the fullness of the buffer memory to maintain a supply of signals for use by the decoder. The decoded signals are supplied to a digital decompression filter for digital reconstruction thereof. A digital to analog converter converts the digital signals to analog form.

24 Claims, 13 Drawing Figures

FIG-2

| | | | | |
|---|---|---|---|---|
| (A) ANALOG INPUT AND OUTPUT | | | | |
| (B) A/D CONVERTER 20-OUTPUT | $f_{n-1}$ (8 bits) | $f_n$ (8 bits) | $f_{n+1}$ (8 bits) | ... $f_{n+i}$ (8 bits) |
| (C) COMPRESSION FILTER 30-OUTPUT | $\Delta_n$ (8 bits) | $\Delta_{n+1}$ (8 bits) | $\Delta_{n+2}$ (8 bits) | ... $\Delta_{n+i}$ (8 bits) |
| (D) ENCODER-40 OUTPUT DECODER-80 INPUT | $H(\Delta_n)$ (1 to 14 bits) | $H(\Delta_{n+1})$ (1 to 14 bits) | $H(\Delta_{n+2})$ (1 to 14 bits) | ... $H(\Delta_{n+i})$ (1 to 14 bits) |
| (E) DECODER-80 OUTPUT | $\Delta_n$ (8 bits) | $\Delta_{n+1}$ (8 bits) | $\Delta_{n+2}$ (8 bits) | ... $\Delta_{n+i}$ (8 bits) |
| (F) RECONSTRUCTION FILTER 90 INPUT | $\Delta_n$ (10 bits) | $\Delta_{n+1}$ (10 bits) | $\Delta_{n+2}$ (10 bits) | ... $\Delta_{n+i}$ (10 bits) |
| (G) D/A CONVERTER 96 INPUT | $f_n$ | $f_{n+1}$ | $f_{n+2}$ | ... $f_{n+i}$ |

| $\Delta_n$ | CODE | APPROXIMATE PROBABILITY | WORD LENGTH |
|---|---|---|---|
| -3 | 00000001 | 0.011 | 8 |
| 3 | 0000001 | 0.012 | 7 |
| else(-4) | 000001 | 0.018 | 6 |
| -2 | 00001 | 0.057 | 5 |
| 2 | 0001 | 0.059 | 4 |
| -1 | 001 | 0.189 | 3 |
| 1 | 01 | 0.188 | 2 |
| 0 | 1 | 0.467 | 1 |

TREE

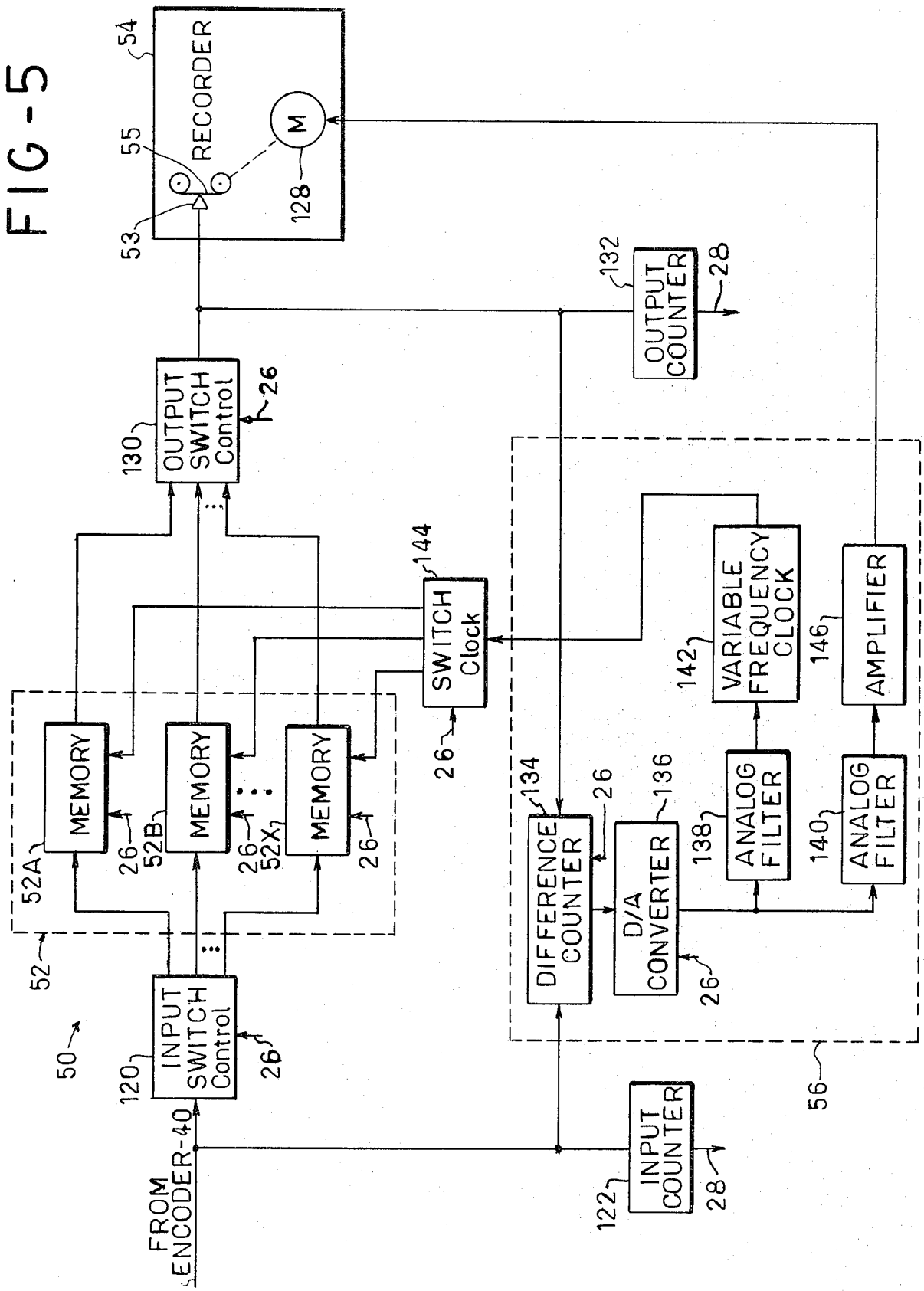

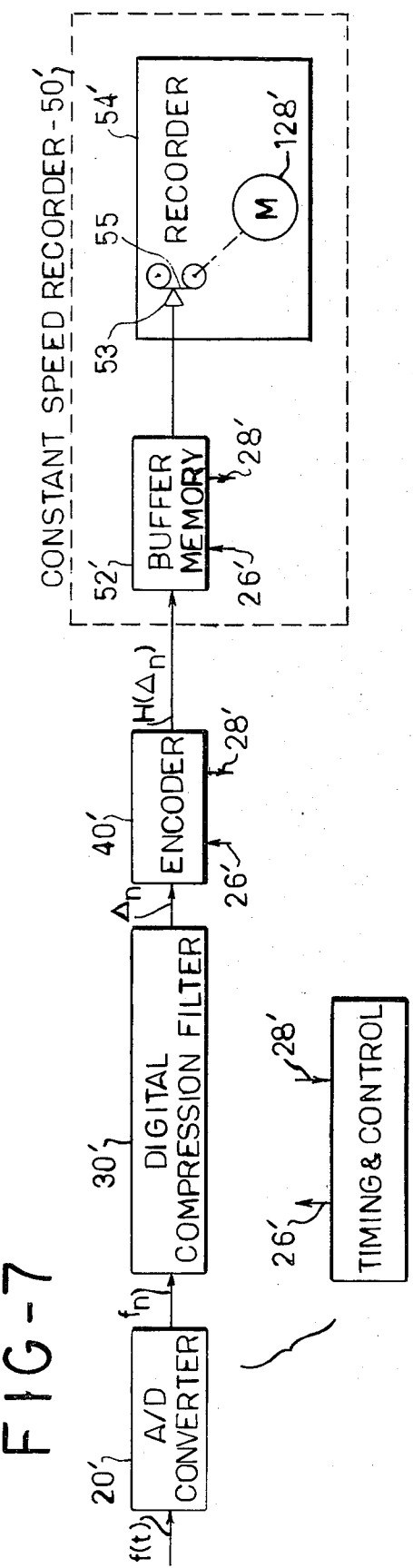
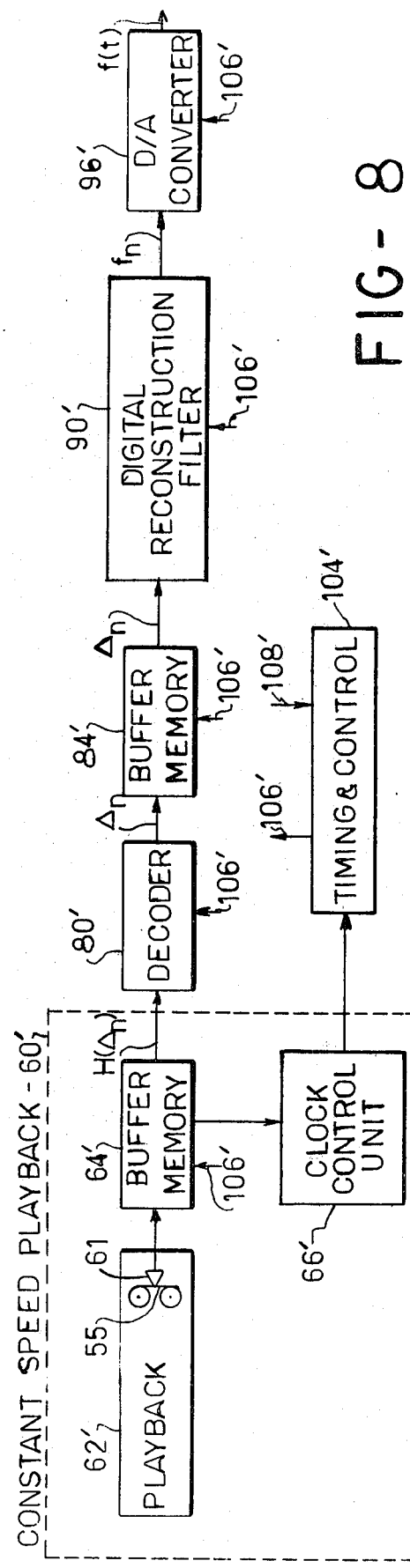

FIG-10

DIGITAL RECORDING AND PLAYBACK METHOD AND APPARATUS

ORIGIN OF THE INVENTION

The Government has rights in this invention pursuant to Contract No. NO1-NS-3-2322.

BACKGROUND OF THE INVENTION

The present invention relates to a digital recording and playback method and system by means of which a maximum amount of information may be recorded in digital form on a recording medium, which information may be faithfully reproduced upon playback.

Analog signals first may be converted to digital form by use of an analog to digital converter, and then recorded. On playback, the digital signals are easily reproduced without error, and then converted to analog form for reproduction of the original analog signals. However, faithful recording and reproduction of many analog signals requires operation at an extremely high bit rate not readily attainable using conventional recording and playback equipment employing a conventional recording medium, such as recording tape, or the like.

Data reduction techniques for reducing the average bit rate of digitized data are known. Those include, for example, the use of compression-decompression filter combinations wherein a compression filter at the recording unit of the system makes periodic estimates of values of the digitized sample signals based on previous, or previous and subsequent values thereof. The difference between an estimated, or predicted, value and a true value of the waveform is calculated. A decompression filter in the playback unit is used to make an identical estimate and, by addition to previous values, find the true value of the waveform. In general, the dynamic range of the difference is smaller than the dynamic range of the original time waveform, so that a smaller average bit rate is required for recording. In addition, further reduction in the average bit rate by encoding of difference signals prior to recording thereof also is known. For example, the use of a truncated Huffman type encoding means for further reducing the average number of bits needed to be recorded is known. A method of reducing the average bit rate by use of a second-order digital compression filter followed by a Huffman encoder is disclosed in an article by U. E. Ruttiman and H. S. Pipberger entitled, "Compression of the ECG by prediction of Interpolation and Entropy Encoding", IEE Transactions on Biomedical Engineering, Vol. BME-26, No. 11, pp. 613-623, Nov. 1979. Also, the recording of encoded digitized ECG signals is disclosed in an article by K. L. Ripley and J. R. Cox, Jr. entitled, "A computer System for Capturing Transient Electrocardiographic Data", *Proc. Comput. Cardiol.*, pp. 439-445, 1976. There, digitized ECG signals are second-differenced using computer software, the second-differenced values are Huffman encoded, and the serial bit stream from the Huffman encoder is stored on disc storage means. With such prior art arrangements employing fixed speed transport of the recording medium, the speed must be sufficient to record the peak bit rates.

Variable speed recording and playback means also are well known. However, they have not been used in conjunction with compression-decompression filter combinations and encoder-decoder combinations such as described above for maximizing the amount of data which may be stored on a recording medium.

SUMMARY OF THE INVENTION

In accordance with the present invention, analog signals to be recorded such as electrocardiographic (ECG), electroencephalographic (EEG), music, or like signals, are converted to sequential digital sample signals of fixed word length, and the digital sample signals are supplied to digital compression filter means for digital compression thereof. Signals from the digital compression filter means are encoded using a code having variable length code words, with the shortest code words being used to encode the most frequently occurring signals from the compression filter means. The encoded signals are written into buffer memory means from which they are read out at a variable rate which is a function of the number of bits contained in said buffer memory. The output from the buffer memory means is supplied to a variable speed recorder for recording of the encoded signals. The recording speed also is made a function of the number of bits contained in said buffer memory. Consequently, the recording speed is proportional to the buffer memory read out rate, whereby the recording density on the recording medium is substantially constant. The ratio of recording speed to buffer memory readout speed may be chosen to provide for maximum bit density on the selected recording medium.

A playback unit for playback of the recorded signals includes a variable speed drive mechanism. The output from the pick-up of the playback unit is supplied to a buffer memory, and the speed of the playback drive mechanism is controlled in inverse proportion to the number of bits written into said buffer memory and not yet read out therefrom. Consequently a supply of signals is maintained in the buffer memory for read out of a decoder at a word rate required by the decoder. The signals then are decoded and the decoded signals are supplied to a digital reconstruction filter. The output from the digital reconstruction filter may be converted to analog form by use of digital to analog converter means.

In a modified form of playback unit embodying this invention, the transport mechanism operates at a uniform rate whereby output bits from the pick-up head of the playback unit are supplied at a substantially uniform bit rate to the buffer memory. With this arrangement, the read out rate from the buffer memory and the word rate of operation of the decoder and digital reconstruction filter are controlled in direct proportion to the number of bits written into said buffer memory and not yet read out therefrom to avoid overflow and emptying of the buffer memory before the end of playback.

BRIEF DESCRIPTION OF THE DRAWINGS

The invention will be better understood from the following description when considered with the accompanying drawings. In the drawings, wherein like reference characters refer to the same parts in the several views:

FIG. 2, A-G, shows an analog waveform and graphic representations of digital signals appearing at various locations in the recording and playback systems of FIGS. 1A and 1B;

FIG. 5 is a block diagram showing details of the variable speed recorder unit shown in FIG. 1A;

FIG. 7 shows in block diagram form a modified form of recording system embodying the present invention;

FIG. 8 shows in block diagram form a modified form of playback system embodying the present invention;

FIG. 10 is a graphic representation of digital signals appearing at various locations in the recording and playback systems shown in FIGS. 7 and 8.

RECORDING SYSTEM

Figure 1A:
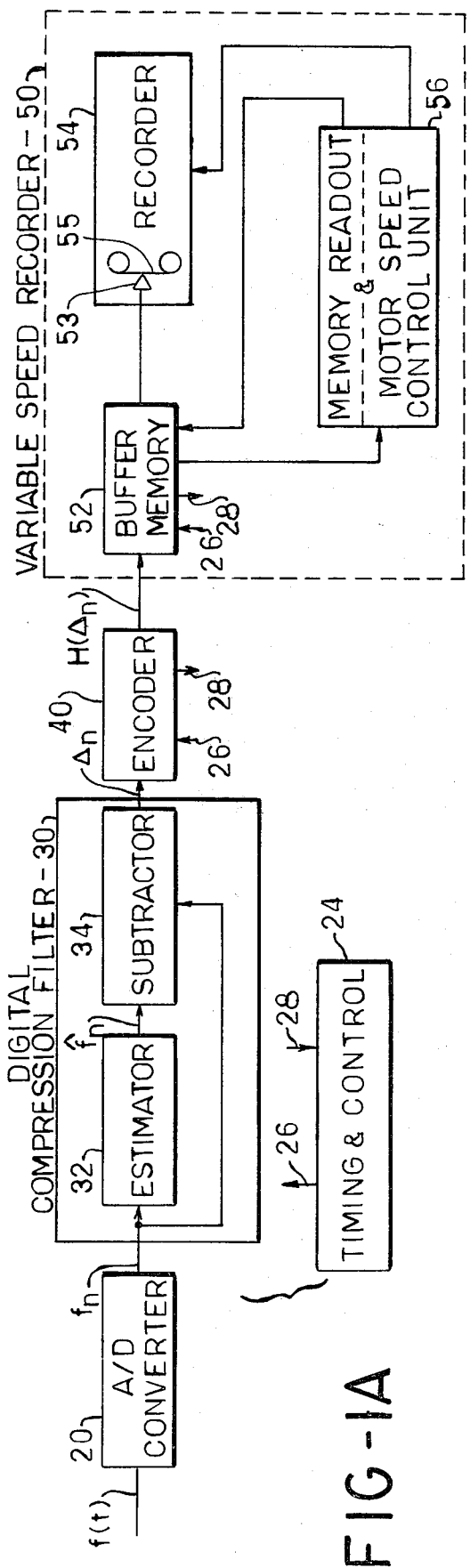
FIGS. 1A and 1B show in block diagram form novel recording and playback systems, respectively, embodying the present invention.

Reference first is made to FIG. 1A wherein the recording unit of a combination recording-playback system embodying the present invention is shown comprising an analog to digital converter (A/D converter) 20 for conversion of an analog input signal f(t) into digital form, the $n^{th}$ sample from the analog to digital converter 20 being identified as $f_n$. At A of FIG. 2, an analog signal 22 is shown which comprises an input to the analog to digital converter 20. The form of the analog to digital converter output is shown at B of FIG. 2. There the A/D converter output is shown comprising samples $f_{n-1}$ through $f_{n+i}$ of equal length words. The analog to digital converter 20 operates at a sampling rate established by control signals from a timing and control unit 24 supplied thereto over timing line 26. As employed, herein, line 26 from the timing and control unit 24 represents a plurality of timing circuit outputs, one or more of which are supplied to the system elements for proper system timing and control. Inputs also are supplied to the timing and control unit over line 28 for control thereof by signals from various other system elements in a manner described in detail hereinbelow. For present purposes, it will be understood that the A/D converter 20 operates in a conventional manner at a fixed sampling rate and with a fixed word length output. For purposes of illustration, an 8 bit word length is assumed.

The digital output from the A/D converter 20 is supplied to a digital compression filter 30 which, for purposes of description only, is shown to include an estimator 32 and subtracting means 34. The estimator 32 provides an estimate of $f_n$, here identified as $\hat{f}_n$, based upon actual samples occuring both before and after the sample $f_n$ to be estimated. Estimators for providing such estimated $\hat{f}_n$ values are, of course, well known. A difference signal $\Delta_n$ is produced by the compression filter 30 comprising the difference between the actual signal input $f_n$ and the estimated signal value $\hat{f}_n$ by subtraction of the estimated value from the actual value at subtracting means 34, as follows:

$$\Delta_n = f_n - \hat{f}_n \quad (1)$$

In the graphic signal representation of the compression filter output, shown at C in FIG. 2, difference signals $\Delta_n, \Delta_{n+1}, \Delta_{n+2}, \ldots \Delta_{n+i}$ are shown. Compression filtering for use with this invention is disclosed in greater detail below under the heading "Digital Compression-Decompression Filter Combination".

The difference signal values $\Delta_n$ from the compression filter 30 are supplied to an encoder 40 employing a truncated Huffman code for encoding the same. Huffman encoding is disclosed in an article by D. A. Huffman entitled, "A Method for the Construction of Minimum Redundancy Codes", *Proceedings of the IRE*, Vol. 40, page 1098, September 1952. Truncated Huffman encoding also is known as disclosed, for example, in the articles mentioned in the Background of the Invention, above. In brief, the Huffman encoding technique makes use of the fact that the compression filter 30 has difference signal outputs, $\Delta_n$, having different probabilities of occurance, and uses this fact to achieve a reduction in the total number of bits in the encoded signal over the input signal. A single code word is assigned to infrequently occuring difference signals, and supplied as a label for the actual difference signal value $\Delta_n$. In FIG. 1A, the encoder 40 output is designated $H(\Delta_n)$ and, at D in FIG. 2, the values $H(\Delta_n)$, $H(\Delta_{n+1})$ etc. represent encoded values of $\Delta_n, \Delta_{n+1}$, etc. The most frequently occurring value of $\Delta_n$ (here zero) is encoded using the shortest code word. A truncated Huffman code is disclosed hereinbelow which is readily implemented using conventional digital computing techniques. For present purposes, it will be understood that the encoder 40 output comprises code words for the most frequently occurring values of $\Delta_n$, together with a combined code word label and actual value of the difference signal $\Delta_n$ for less frequently occurring values of $\Delta_n$. In the graphic signal representation of the encoder 40 output, shown at D in FIG. 2, encoded difference signals $H(\Delta_n)$, $H(\Delta_{n+1}) \ldots H(\Delta_{n+i})$ are shown, which signals vary in word length between, say, 1 and 14 bits. It will be seen, then, that although the encoded difference signals are produced at a substantially constant word rate, the stream bit rate varies over a wide range. If a fixed speed recoder were employed to record these signals, the recorder speed would have to be sufficient to record the peak bit rates occurring when the 14 bit code word label and actual difference signal value are produced at the encoder output. Encoding is discussed in greater detail below under the heading "Encoding-Decoding".

Figures 3, 4:
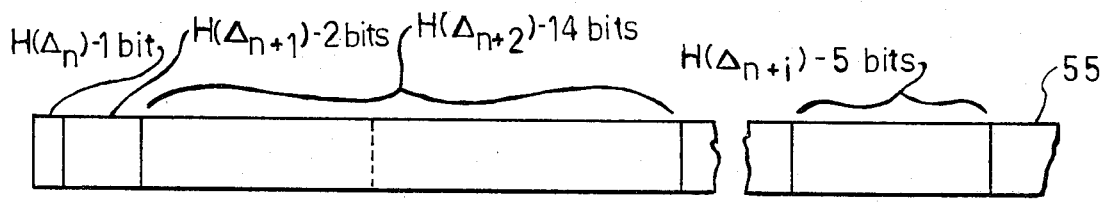
FIG. 3 is a schematic illustration showing the density at which the compressed and encoded digital signals may be recorded on a recording medium.
FIG. 4 is a table showing a truncated Huffman code which may be used in the practice of this invention.

The compressed and encoded signals $H(\Delta_n)$ from the encoder 40 are recorded by use of a variable speed recorder unit 50, which unit is described in detail hereinbelow under the heading "Variable Speed Recorder". For present purposes, it will be seen that the recorder unit includes buffer memory means 52 for temporary storage of the encoded signals as they are produced by the encoder 40. The encoded signals are read out of buffer memory 52 at a variable rate and supplied to the recording head 53 of recorder 54 for recording on a movable recording medium 55, such as a recording tape, or the like. The relative speed of the recording head and recording medium also is variable. A memory readout and motor speed control unit 56 controls both the readout rate from memory 52 and the recording speed. The control unit 56 is responsive to the number of bits contained in the buffer memory means 52 (i.e. the number read into the buffer memory less the number read out therefrom) for control of both the buffer memory readout rate, and the recording speed, in proportion thereto. Using this variable speed recording means, variations in the recording density are substantially reduced as compared, say, to the recording density which would result in using a fixed speed transport system. The ratio of the memory read out rate and recording speed may be selected for maximum recording density on the selected recording medium; the absolute maximum employable recording density being limited, of course, by the quality of the recording equipment employed including the recording head and recording medium. In FIG. 3 of the drawings, to which reference is made, the recording tape 55 with encoded difference signals $H(\Delta_n)$, $H(\Delta_{n+1})$, $H(\Delta_{n+2})$ . . . and $H(\Delta_{n+i})$ which are 1, 2, 14 and 5 bits in length, respectively, is shown. Even though the different length encoded difference signals are produced at a substantially constant word rate, they are recorded with substantially a constant bit density on the tape; with the words being recorded immediately adjacent each other.

PLAYBACK SYSTEM

Figure 1B:
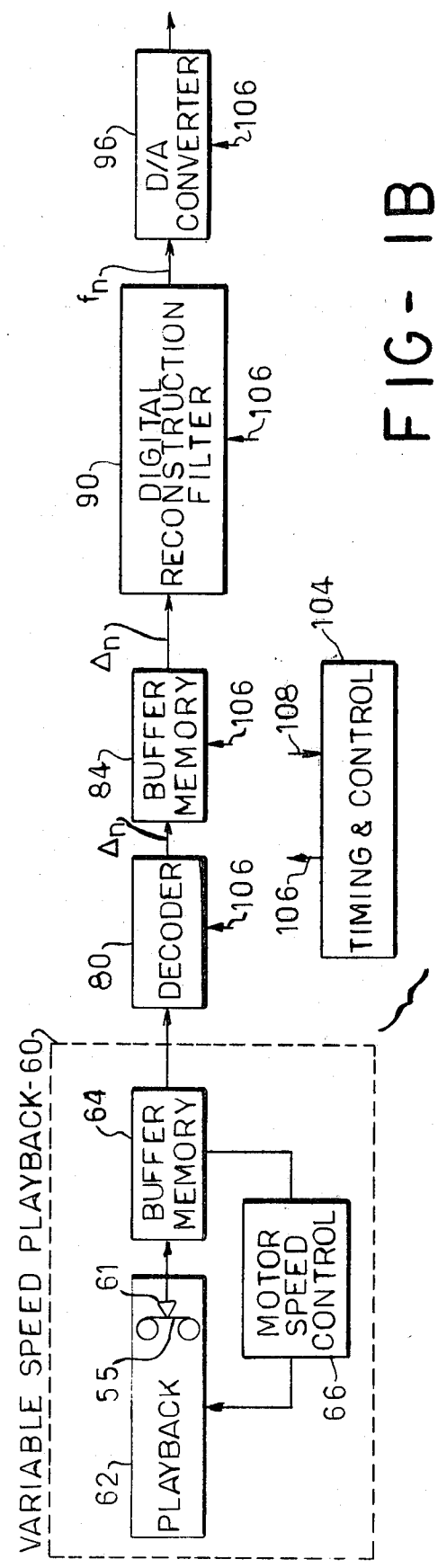

Signals recorded by the above-described recording system are reproduced using the playback system shown in FIG. 1B. There, the playback system is shown to include a variable speed playback unit 60 comprising a pick up head 61 and drive mechanism for producing relative movement between the recorded medium 55 and pick up head 61 included in the block 62 labeled PLAYBACK. The signals from the pick up head 61 are supplied to a buffer memory 64. A motor speed control unit 66 controls the transport speed of the playback device 62 in proportion to the number of bits contained in the buffer memory 64 (i.e. the number of bits read into the buffer memory less the number read out therefrom); the motor speed control unit being responsive to the number of bits in the buffer memory in a manner described in detail below.

From the buffer memory 64, the encoded signals are fed to a decoder 80 for decoding the truncated Huffman encoded signals. At the decoder 80, the Huffman code words are converted to the original difference signals $\Delta_n$. Where the Huffman code word comprises a labeled actual difference signal, the label is stripped therefrom, and the actual difference signal without the label is supplied to the decoder output. The decoder input and output signals are depicted at D and E, respectively, in FIG. 2. Decoding is discussed in greater detail below under the heading "Encoding-Decoding".

The difference signals $\Delta_n$ from the decoder 80 are supplied to a reconstruction, or decompression, filter 90, through a small, one word, buffer memory 84. The decoder output signals are produced at substantially constant, but slightly varying rates, and the small buffer memory 84 is included to accommodate the input rate requirements of the reconstruction filter 90. From the difference signal values, actual signal values $f_n$ for every sample are determined at the reconstruction filter 90. The reconstruction filter input signal is depicted at F of FIG. 2. Reconstruction filtering for use with this invention is disclosed in greater detail below under the heading "Digital Filter Combination".

A digital to analog converter (D/A Converter) 96 converts the actual signal samples $f_n$ from the digital reconstruction filter 90 to analog form, and any desired use may be made of the analog signals. The D/A converter input signal is depicted at G of FIG. 2. A playback timing and control unit 104 supplies timing signals to the various receiver elements over line 106 for proper timing of the playback operation. Also, control signals for the unit 104 are supplied thereto over line 108 from various elements of the playback system for proper control thereof.

DIGITAL COMPRESSION-DECOMPRESSION FILTER COMBINATION

Digital compression filter 30 and reconstruction filter 90 combinations for implementing the above-described signal compression and decompression functions are well known and any suitable combination thereof may be utilized in the present invention.

UNSTABLE COMBINATION

As noted above in the description of FIG. 1A, the digital compression filter 30 includes an estimator 32 having an output comprising an estimated sample value $\hat{f}_n$ based upon actual samples $f_{n-1}$ and $f_{n+1}$ occurring before and after the sample $f_n$ to be estimated. Often prior art estimators are used which provide an output, $$\hat{f}_n = a_1 f_{n+1} + a_2 f_{n-1} \tag{2}$$

where the coefficients $a_1$ and $a_2$ are chosen to minimize the mean square error of the difference $\Delta_n$, where $\Delta_n = f_n - \hat{f}_n$, as noted in equation (1), above. For compression of ECG signals, for example, the coefficients $a_1$ and $a_2$ are substantially optimum when they equal 0.5. Consequently, for $a_1 = a_2 = 0.5$, equations (1) and (2) may be combined to give $$\Delta_n = 0.5[f_{n+1} - 2f_n + f_{n-1}] \tag{3}$$
$$= 0.5 f_{n+1} - f_n + 0.5 f_{n-1}$$

It will be seen that the quantity inside the brackets is the second difference of $f_n$ and, since the sample rate is greater than the Nyquist rate, the second difference is equivalent to the second derivative. Digital data compression systems which employ such a double difference compression filter include a reconstruction filter of the double integration type in the receiver unit for decoding such double difference signals. Thus, where a prior art double difference type compression filter 30 is employed in the system, an associated double integration type reconstruction filter 90 would be employed therewith. In such a case, the reconstruction filter 90 would operate to make use of the following equations:

$$f_{n+1} = \frac{f_n}{a_1} - \frac{a_2}{a_1} f_{n-1} \tag{4}$$

$$= \frac{f_n - \Delta_n}{a_1} - \frac{a_2}{a_1} f_{n-1} \tag{5}$$

From equation (5), which is recursive, it will be apparent that two adjacent sample values together with the value of $\Delta_n$ are required for the solution thereof. Thereafter, only the values of $\Delta_n$ are required. Similar algorithms can be derived for any number of coefficients.

The above described prior art double difference-double integration filter combination is unstable such that bit errors in the passage of data between the compression and reconstruction filters result in a random ramp from the reconstruction filter which is added to signals following the bit error. It will be apparent, then, that error free operation, or the use of error recovery means, is required for proper operation of such a compression-reconstruction filter combination.

As noted above, equation (5) requires two successive values of $f_n$ as initial conditions. If some $\Delta_n$'s are lost after one or more bit errors, the reconstructed $f_n$ as calculated by equation (5) will differ from the true $f_n$ by a ramp of unknown slope. Where the system is not subject to bit errors, the use of such compression-decompression filter combination is acceptable. A compression-decompression filter combination which is stable may be employed, in the novel system of this invention, and one such stable combination now will be described.

STABLE COMBINATION

The Z-transform of the double difference equation $\Delta_n = 0.5 \, (f_{n+1} - 2f_n + f_{n-1})$; equation (3) above, is $$\frac{\Delta(Z)}{f(Z)} = 0.5 \, (Z - 2 + Z^{-1}) \quad (6)$$

$$= 0.5Z \, (1 - 2Z^{-1} + Z^{-2})$$

$$= 0.5 \frac{(1 - Z^{-1})(1 - Z^{-1})}{Z^{-1}}$$

Consider the following modification of equation (6):

$$\frac{\Delta Z}{f(Z)} = 0.5 \frac{(1 - aZ^{-1})(1 - aZ^{-1})}{Z^{-1}} \quad (7)$$

$$= 0.5 \, (Z - 2a + a^2 Z^{-1})$$

The corresponding difference equation is:

$$\Delta_n = 0.5 \, (f_{n+1} - 2af_n + a^2 f_{n-1}) \quad (8)$$
$$= 0.5 f_{n+1} - f_n + 2^{-m} f_n + 0.5 f_{n-1} -$$
$$2^{-m} f_{n-1} + 2^{-2m-1} f_{n-1}$$

where:
$a = 1 - 2^{-m}$ and
$m =$ an integer $> 0$

In the generation of $\Delta_n$, using either equation (3) or equation (8), it will be understood that an arithmetic and logic unit, ALU, may be employed for performing the necessary operations. Necessary multiplication operations, for example, may be done by shifting in the ALU, which, of course, may be performed at high speed. From equation (8) for example, it will be seen that sample signals are multiplied by $2^{-m-1}$ and $2^{-m}$, simply accomplished in the ALU by a shift of the indicated sample signals $-m-1$ and $-m$ spaces, respectively, toward the least significant bit position. The $f_{n+1}$, $f_n$ and $f_{n-1}$ signals simply are shifted the indicated number of spaces, and the indicated additions and subtractions are performed in the generation of the difference signal $\Delta_n$.

The inverse of equation (8) is:

$$\frac{f(Z)}{\Delta(Z)} = \frac{2Z^{-1}}{(1 - aZ^{-1})(1 - aZ^{-1})} \quad (9)$$

and the corresponding difference equations are:

$$y_n = 2\Delta_n + ay_{n-1} = 2\Delta_n + y_{n-1} - 2^{-m} y_{n-1} \quad (10)$$

$$f_n = y_n + af_{n-1} = y_n + f_{n-1} - 2^{-m} f_{n-1} \quad (11)$$

Since $$y_{n-1} = af_{n-2} - f_{n-1},$$

the starting equations are:

$$y_3 = 2\Delta_3 - af_2 + a^2 f_1 \quad (12)$$

$$f_3 = y_3 + af_2 \quad (13)$$

It may be shown that:

$$y_n = 2 \sum_{i=0}^{n-3} a^i \Delta_{n-i} + (a^n f_1 - a^{n-1} f_2) \quad (14)$$

$$f_n = \sum_{i=0}^{n-3} a^i y_{n-1} + a^{n-2} f_2 \quad (15)$$

When $a > 1$ the error due to incorrect values of $f_1$ and $f_2$ will die out faster than $a^n$. With a proper choice of m, this can be rapid. A value of m between, say, 2 to 6 is preferred.

There is no round-off error if the arithmetic word length is $2m+2$ bits longer than the input word length. Equations (14) and (15) make it clear why the prior art double integrator ($a=1$) adds a random ramp if incorrect values of $f_1$ and $f_2$ are supplied to the reconstruction filter. With the filter combinations, the output from the decompression filter 90 is identical to the input to the compression filter 30 when there are no intermediate errors. Consequently, the recording and playback is without distortion under error-free conditions. By making m large, the compression-decompression filter combination of the present invention may be made to function as close as desired to the double-difference, double integration scheme.

The transfer function of the compression filter that is given in equation (7) contains two zeros on the real axis of the Z-plane, and the transfer function of the corresponding reconstruction filter contains two poles located at the same point on the real axis. Efficient compression can be obtained even when the zeros are not co-located; i.e., a double zero in the compression filter transfer function is not necessary. The zeros can be at different points on the real axis. There must be a pole in the reconstruction filter transfer function at points identical to the location of the zeros.

The difference equations for such a compression filter are:

$$y_n = 0.5 f_n - 0.5 f_{n-1} + 2^{-m_1 - 1} f_{n-1} \quad (16)$$

$$\Delta_n = y_n - y_{n-1} + 2^{-m_2} y_{n-1} \quad (17)$$

The difference equations for the reconstruction filter are:

$$y_n = 2\Delta_n + y_{n-1} - 2^{-m_1} y_{n-1} \quad (18)$$

$$f_n = y_n + f_{n-1} - 2^{-m_2} f_{n-1} \quad (19)$$

where $m_1$ and $m_2$ are positive integers.

The bandwidth of this latter reconstruction filter should be the same as the bandwidth of the filter whose transfer function is given in equation (9) for equivalent compression and recovery time.

Good efficiency also may be obtained with two complex zeros in the transfer function of the compression filter. The difference equation then is:

$$\Delta_n = f_n - 2f_{n-1} + 2^{-m_1 + 1} f_{n-1}$$
$$+ f_{n-2} - 2^{-m_1 + 1} f_{n-2}$$
$$+ 2^{-2m_1} f_{n-2} + 2^{-2m_2} f_{n-2} \quad (20)$$

The equation for the corresponding reconstruction filter is:

$$f_n = \Delta_n + 2f_{n-1} \\ -2^{-m_1+1}f_{n-1} - f_{n-2} \\ +2^{-m_1+1}f_{n-2} - 2^{-2m_1}f_{n-2} \\ -2^{-2m_2}f_{n-2} \quad (21)$$

where $m_1$ and $m_2$ again are positive integers.

It will be apparent that equations (16) through (21) are readily implemented using conventional digital techniques.

ENCODING-DECODING

Encoders 40 and decoders 80 for implementing the Huffman code are well known and require no detailed description. As is well understood, the Huffman code is a "unique" code, i.e. one with the property that two or more code words cannot be placed in sequence to generate another member of the code-word set. This property makes it possible to find the beginning and end of each code word when the word length is variable without an end-of-word symbol.

A truncated Huffman code which may be used in the illustrated system is shown in the table of FIG. 4. The difference signals, $\Delta_n$, which occur most frequently are assigned a code word. Where the input to the system comprises a digitized ECG signal, and a digital compression filter of the above-described type is employed, the probability of $\Delta_n$ comprising a value of between +3 and −3 is, approximately, 0.98. These difference signals are assigned different length code words, with the most frequently occurring difference signal being assigned the shortest code word. All other difference signals outside the range of ±3 are identified as else in the table, and these are assigned a code word which, as described above with reference to FIG. 2, comprises a label for the actual difference value $\Delta_n$ which subsequently is recorded. With the present system, the recording of the actual $\Delta_n$ value contributes approximately 0.16 bits to the average per symbol (about 10%). However, this is not 10% added to the untruncated Huffman code bit rate, because the code words in the latter code that are assigned to the $\Delta_n$'s that make up else in the truncated code will be no longer than the word that indicates that else has occurred in the truncated code.

In FIG. 4, the approximate probability of occurance of the difference signals $\Delta_n$ is shown to range from 0.467 maximum to 0.011 minimum. The illustrated code word set comprises a 1 bit in the least significant bit position. Any other bit position comprises a zero bit. Simple coding and decoding hardware may be used in implementing the code. The decoder can be represented by the tree included in FIG. 4, where the left branches represent 0's and right branches 1's. The final branches, which are all 1's in this case, indicate the decoded word. The starting bit is entered at the bottom of the tree and the branches are followed until a final branch is reached, then the three is reentered at the bottom.

VARIABLE SPEED RECORDER

Reference now is made to FIG. 5 of the drawings wherein there is shown details of a variable speed recorder 50, of a type which may be used in the present system. The buffer memory 52 included therein comprises a plurality of read/write memories, shift registers, or the like. For present purposes a plurality of read/write memory units 52A, 52B . . . and 52X are shown. The variable length encoded signals $H(\Delta_n)$ are supplied to the memory units through an input switch 120. Address inputs for the input switch 120 for control thereof are supplied thereto over line 26 from timing and control unit 24 (shown in FIG. 1A). The bit output from the encoder 40 is counted as by use of a counter 122, which count is supplied to the timing and control unit 24. The input bit count information is used to control the switch 120, in a manner such that when one of the memory units 52A, 52B, etc. is filled, the input switch 120 is actuated to switch the encoder output to the next succeeding memory unit. When the last memory unit is filled, the input switch is returned to a starting position to repeat the storage of signals in successive memory units. Address inputs and switching of the chip enable and/or, read/write inputs of the memory units also are under control of the timing and control unit 24 for writing of the encoder output into the proper memory locations. The encoded signals from the encoder 40 are written into memory as they are produced by the encoder; the bit rate from the encoder varying widely depending upon the length of the code words produced thereby.

For purposes of illustration, the recording device 54 is shown comprising a tape recorder which includes a tape transport mechanism for moving the recording tape 55 relative to the recording head 53. A variable speed motor 128 drives the tape at a rate dependent upon the number of bits contained in the buffer memory, in a manner described below. Encoded difference signals contained in the buffer memory are read out therefrom to the recording head 53 through an output switch 130. Address inputs for the output switch 130 are supplied thereto over line 26 from the timing and control unit 24. The bit output from the switch 130 is counted by an output counter 132, which count is supplied to the timing and control unit 24. The output bit count information is used to control the output switch 130 in a manner such that when data for one of the memory units has been completely read out therefrom, the output switch 130 is actuated for reading from the next memory unit. Of course, bits are read out from a memory unit only after said unit has been completely filled. Address inputs and switching of the chip read/write inputs of the memory units for reading from the proper memory unit and from the proper memory location are supplied over line 26 from the timing and control unit 24. Buffer memories of this general type which include a plurality of individual memory units together with input and output switches for individual control of the unit into which data is written and the unit from which data is read, respectively, are of course, well known.

In accordance with the present invention, the rate at which bits are read out of the buffer memory 52, and the rate at which the recording tape 55 is transported past the recording head 53 are controlled in a manner to provide for relatively uniform bit density recording on the tape. The ratio of memory read out rate to tape transport rate may be selected for recording with substantially maximum possible bit density on the tape 55. Both the rate at which bits are readout from the buffer memory 52, and the rate at which the motor 128 is operated, are directly proportional to the difference in the number of bits written into the buffer memory means 52 and the number read out therefrom. It here will be noted that in the present specification and claims the term "directly proportional" simply means the opposite of "inversely proportional", and does not otherwise define the functions by which the rates are proportional to the fullness of the buffer memory means. In particular, the term "directly" does not limit operation to a straight line function. With the present invention, buffer memory read out rate increases and the motor speed increases with an increase in the number of bits written into the buffer memory means but have not yet been read out therefrom. As the fullness of the buffer memory means decreases, the buffer memory read out rate and motor speed both decrease.

As seen in FIG. 5, the memory read out and motor speed control unit 56 comprises a difference counter 134 having one input responsive to the number of bits written into the buffer memory unit 52, a second input responsive to the number of bits read out of the buffer memory unit, and an output which is a measure of the difference therebetween. Obviously, the difference counter may comprise separate input and output counters, such as the counters 122 and 132, for counting bits written into the buffer memory and bits read out therefrom, respectively, together with means for subtracting the count inputs, to provide a measure of the number of bits contained in the buffer memory.

A digital control signal is obtained from the difference counter output, which signal is converted to analog form by a digital to analog converter 136. The analog control signal from the digital to analog converter is supplied to first and second analog filters 138 and 140 comprising low pass filters. The output from the one filter 138 is supplied to a variable frequency read out clock 142 for control of the clock frequency. The clock frequency is increased and decreased with an increase and decrease, respectively, in the difference in the number of bits written into said buffer memory means and the number of bits read out therefrom. The clock output from variable frequency clock 142 is supplied to the chip enable input of one of the memory units 52A, 52B . . . 52X through a switch 144, which switch is controlled by an output from the timing and control unit 24 supplied thereto over line 26. The switch 144 is operated in synchronism with the output switch 130 such that signals read out from a selected memory unit are connected through the switch 130 to the recording head 53. Address inputs and switching of the chip read/write input for reading from proper memory locations are under control of the timing and control unit 24. When all bits stored in one memory unit are read out therefrom, the switches 130 and 144 are simultaneously actuated for read out from the next succeeding memory units. It will be seen then, that bits are written into said buffer memory means 52 at a rate dependent upon the rate at which the encoded difference signal bits are supplied thereto from the encoder 40, and are read out from said buffer memory means at a rate dependent upon the difference in the number of encoded difference signal bits written into and the number read out therefrom.

As noted above, the control signal output from the digital to analog converter 136 is supplied to a second analog filter 140. The output from filter 140, in turn, is amplified by an amplifier 146, and the amplified signal is connected to the variable speed tape drive motor 128 for energizing the same. The speed, or rate, at which the motor operates and, thereby, the rate at which the recording tape 55 is moved relative to the recording head 53 is controlled by the amplifier output in a manner such that recording tape speed increases and decreases with an increase and decrease, respectively, in the difference in the number of encoded difference signal bits written into the buffer memory means 52 and the number read out therefrom.

Figure 5A:
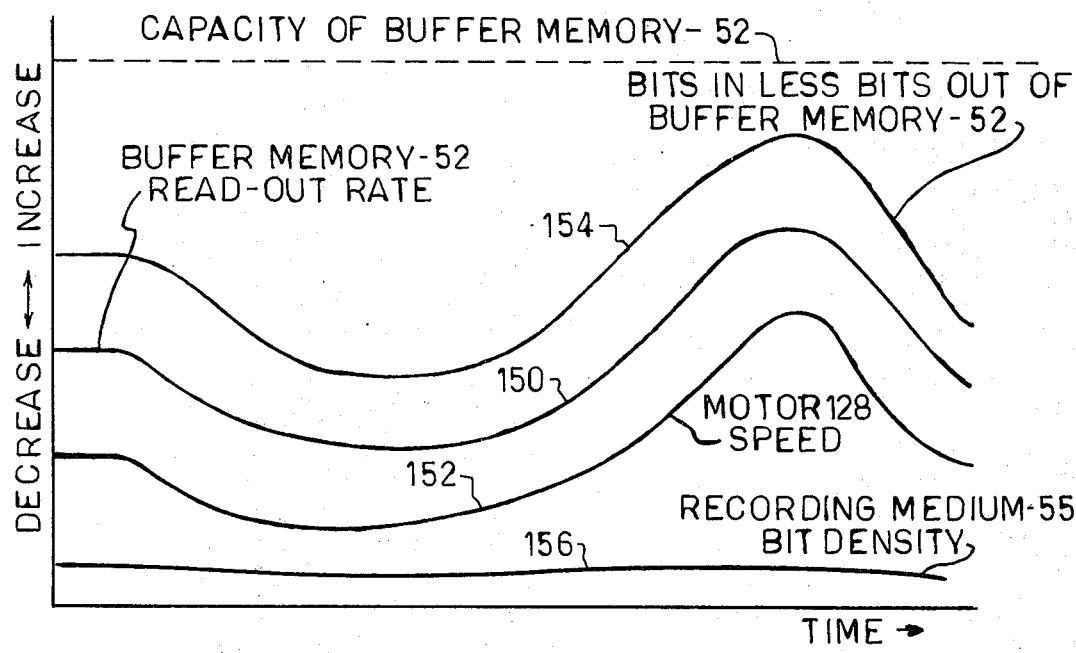
FIG. 5A is a graph for use in explaining operation of the recorder shown in FIG. 5.

Reference now is made to FIG. 5A wherein the graph depicted therein illustrates control of the buffer memory 52 read out rate (curve 150) and the motor 128 speed (curve 152) in direct proportion to the number of bits written into the buffer memory means less the number of bits read out therefrom (curve 154). By operating in this manner, a substantially constant, or uniform, bit density is provided on the recording tape 55 as indicated by the recording tape bit density curve 156. As noted above, the ratio of the buffer memory read out rate and motor speed may be selected, as desired, and, obviously, they may be selected to provide for recording with maximum bit density on the recording medium 55.

VARIABLE SPEED PLAYBACK

Figure 6A:
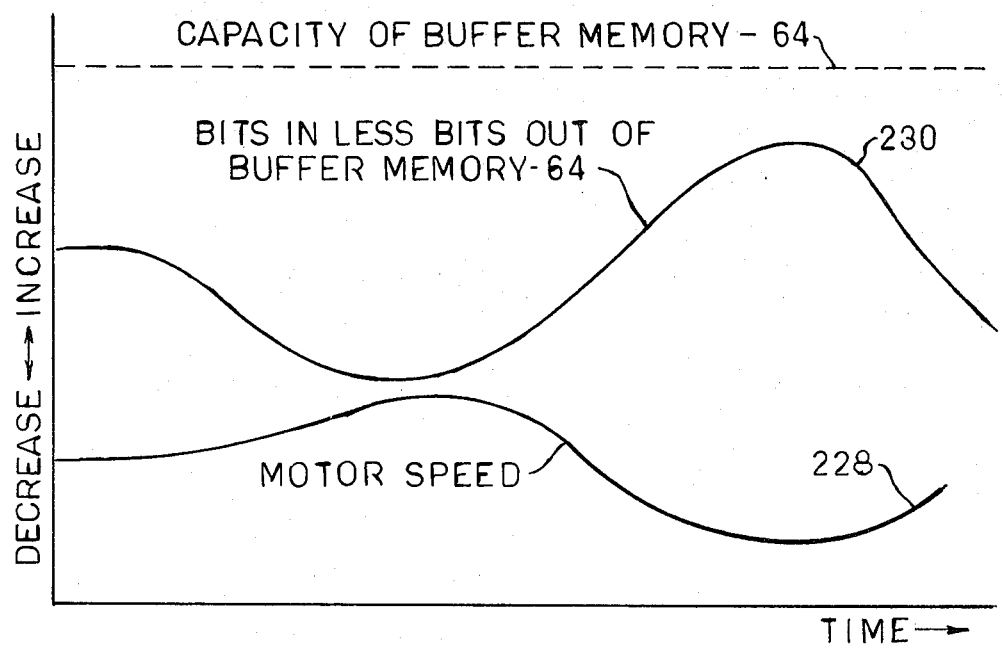
FIG. 6A is a graph for use in explaining operation of the playback unit shown in FIG. 6.
Figure 6:
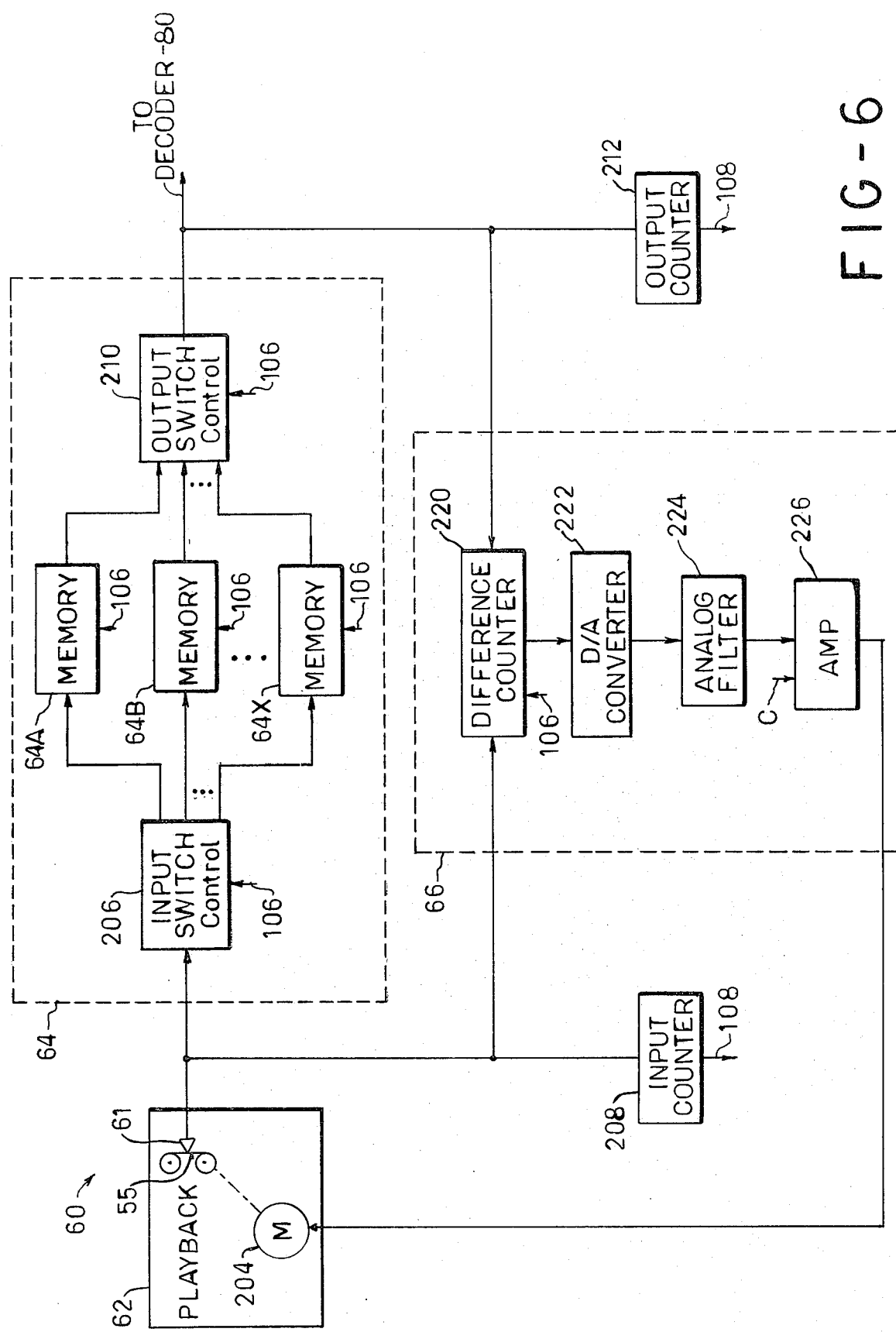
FIG. 6 is a block diagram showing details of the variable speed playback unit shown in FIG. 1B.

Reference now is made to FIG. 6 of the drawings wherein there are shown details of a variable speed playback unit 60 of a type which may be employed in the present system. For playback, the recording medium 55 upon which the encoded difference signals were recorded using the variable speed recording system 50 is mounted on the transport mechanism included in the playback device 62. The recording medium 55 is moved relative to the pickup head 61 by means of a variable speed motor 204 energized by an output from the motor speed control unit 66. The speed at which the recording medium 55 is moved is inversely related to the fullness of the buffer memory means 64 to which the output from the pickup head 61 is supplied.

The buffer memory 64 may be of the same type as the buffer memory 52 included in the recording system and, for purposes of illustration is shown to comprise a plurality of read/write memory units 64A, 64B . . . and 64X. The variable length encoded signals $H(\Delta_n)$ from pickup head 61 are supplied to the memory units through an input switch 206. Address inputs for the input switch 206 for control thereof are supplied to the switch over line 106 from the timing and control unit 104, shown in FIG. 1B. The output from the pick-up head 61 also is supplied to an input counter 208 for counting the number of bits supplied to the buffer memory 64. The input bit count from input counter 208 is supplied to the timing and control unit 104 over line 108, which input bit count information is used to control the input switch 206 in a manner such that when one of the memory units 64A, 64B, etc. is filled, the input switch 206 is actuated to switch the output from the pick up head 61 to the next succeeding memory unit. When the last unit is filled, the input switch 206 is returned to a starting position to repeat the storage of signals in succeeding memory units. Address inputs and switching of enable and/or read/write inputs for the memory units also are under control of the timing and control unit 104 for writing into and reading from the proper memory locations. The encoded signals from the pick up head 61 are written into the buffer memory as they are produced at the pick up head. Of course, the rate at which bits are supplied from the pick up is dependent upon the rate at which the recording medium 55 is driven relative to the pick up head by motor 204.

Encoded difference signals contained in the buffer memory units are read out therefrom to the decoder 80 through an output switch 210. Address inputs for the output switch are supplied thereto over line 106 from the timing and control unit 104. The bit output from the switch 210 is counted by an output counter 212, which count is supplied to the timing and control unit 104 over line 108. The output bit count information is used to control the output switch 210 in a manner such that when data from one of the memory units 64A, 64B . . . 64X has been completely read out therefrom, the output switch 210 is actuated for reading from a succeeding memory unit. Line 106 from timing and control unit 104 also provides the necessary memory address inputs and switching of enable and/or read/write inputs for the memory units 64A, 64B . . . 64X for proper timing of the above-described memory read operation.

As noted above, the encoded difference signals $H(\Delta_n)$ vary widely in length, here, varying from 1 to 14 bits. The decoder 80 operates at a substantially constant bit rate for production of difference signals $\Delta_n$ at a substantially constant rate in response to the variable length encoded difference signals supplied thereto. The buffer memory means 64, from which the variable length encoded difference signals are obtained for decoding is maintained partially filled to ensure an adequate supply of input signals for the decoder 80. Such a supply of encoded difference signals simply is maintained by controlling the rate at which the recording medium 55 is transported relative to the pick up head 61, thereby effectively controlling the rate at which bits are read into the buffer memory means 64 from the recording medium.

The speed of the tape transport motor 204 may be controlled in substantially the same manner as that of the motor 128 in the recording unit. In FIG. 6, the motor speed control unit 66 is shown to include a difference counter 220 which is provided with inputs from both the input to and the output from the buffer memory means 64, and which has an output responsive to the difference in the counts of the two inputs. The difference counter output, therefore, provides a measure of the difference in the number of bits written into the buffer memory means 64 and the number read out therefrom.

The digital difference counter 220 output is converted to analog form by means of an analog to digital converter 222. The analog signal output from the converter 222 is filtered by a low pass filter 224, and supplied to one input terminal of a difference amplifier 226. The other amplifier input terminal is supplied with a constant voltage, C, and the amplifier output is related to the difference between the two inputs in a manner such that the amplifier output decreases with an increase in the analog signal supplied thereto from filter 224, and increases with a decrease in said analog signal. The amplifier output is connected to the variable speed motor 204 for energizing the same. With this arrangement the speed, or rate, at which the motor operates is inversely proportional to the difference in the number of encoded difference signal bits written into the buffer memory means 64 and the number read out therefrom.

Referring to the graph of FIG. 6A, this relationship between the motor speed and fullness of the buffer memory means 64 is illustrated. In FIG. 6A, the motor speed curve is identified by reference numeral 228, and the curve for the number of bits in less the number of bits out of the buffer memory means 64 is identified by reference numeral 230. By operating in this manner, different length encoded difference signals $H(\Delta_n)$ are immediately available for decoding by decoder 80 at a substantially constant word rate from the buffer memory means 64.

A modified form of recording system for recording encoded difference signals $H(\Delta_n)$ on a recording medium with a substantially constant bit density is shown in FIG. 7, to which figure reference now is made. The recording system includes an analog to digital converter 20', digital compression filter 30' and encoder 40' of the same type as a/d converter 20, filter 30 and encoder 40 shown in FIG. 1A and described above. Different length encoded difference signals $H(\Delta_n)$ from the encoder 40' are produced at a substantially constant word rate in the manner described above with reference to FIG. 1A. In the FIG. 7 arrangement, a constant speed recording unit 50' is used to record the encoded difference signals. The encoded difference signals $H(\Delta_n)$ from the encoder 40' are supplied to the recording head 53 of recorder 54' through a large buffer memory 52' for recording on the recording medium 55, which medium is driven at a constant, uniform, rate past the recording head by use of a constant speed motor 128'. The encoded difference signals $H(\Delta_n)$ are written into the buffer memory 52' as they are produced by the encoder 40', and are read out therefrom to the recording head at a constant bit rate, all under control of timing and control signals supplied thereto over line 26' from timing and control unit 24'. In operation, the buffer memory 52' may be at least partially filled with encoded difference signals before proceeding to read the signals out therefrom at a constant bit rate. The memory must be sufficiently large to avoid overflow or emptying during recording. It will be apparent, then, that the different length encoded difference signals are recorded with a substantially constant bit density on the recording medium. The ratio of the read out rate from the buffer memory 52' and the speed of motor 128' may be selected for recording with a maximum bit density on the recording medium 55. It will be apparent that recording with the same bit density as provided by the system shown in FIG. 1A is possible using the system of FIG. 7. (See, for example, FIG. 3.)

A modified form of playback system embodying the present invention for playing back signals recorded on the recording medium 55 by means of either of the above-described recording systems is shown in FIG. 8, to which figure reference now is made. This system includes a constant speed playback unit 60' which includes a tape transport mechanism for moving the tape 55 at a constant speed relative to the pick-up head 61. The output from the pick-up head 61 is supplied to a decoder 80' through buffer memory means 64'. A clock control unit 66' is included in the playback system, which unit has an output related to the number of bits read into the buffer memory means 64' less the number read out therefrom. Unlike the control unit 66 included in the playback system of FIG. 1B, the output from the control unit 66' controls clock means in the timing and control unit 104' which, in turn, controls the rate at which the system operates to decode and decompress the encoded difference signal from the buffer memory means 64'. Thus, with the present arrangement, the rate at which bits are read-out from the buffer memory, 64', and the rate of operation of the decoder 80', buffer memory 84', digital reconstruction filter 90' and digital to analog converter 96' are under control of the output from the clock control unit. The decoder 80', buffer memory 84' digital reconstruction filter 90' and D/A converter 96' may be of the same types as corresponding elements shown in FIG. 1B and described in detail above. However, instead of operating at a substantially constant word rate, they are operated at a variable word rate to prevent overflow and emptying of the buffer memory means 64' during playback before the end of the recording.

Figure 9:
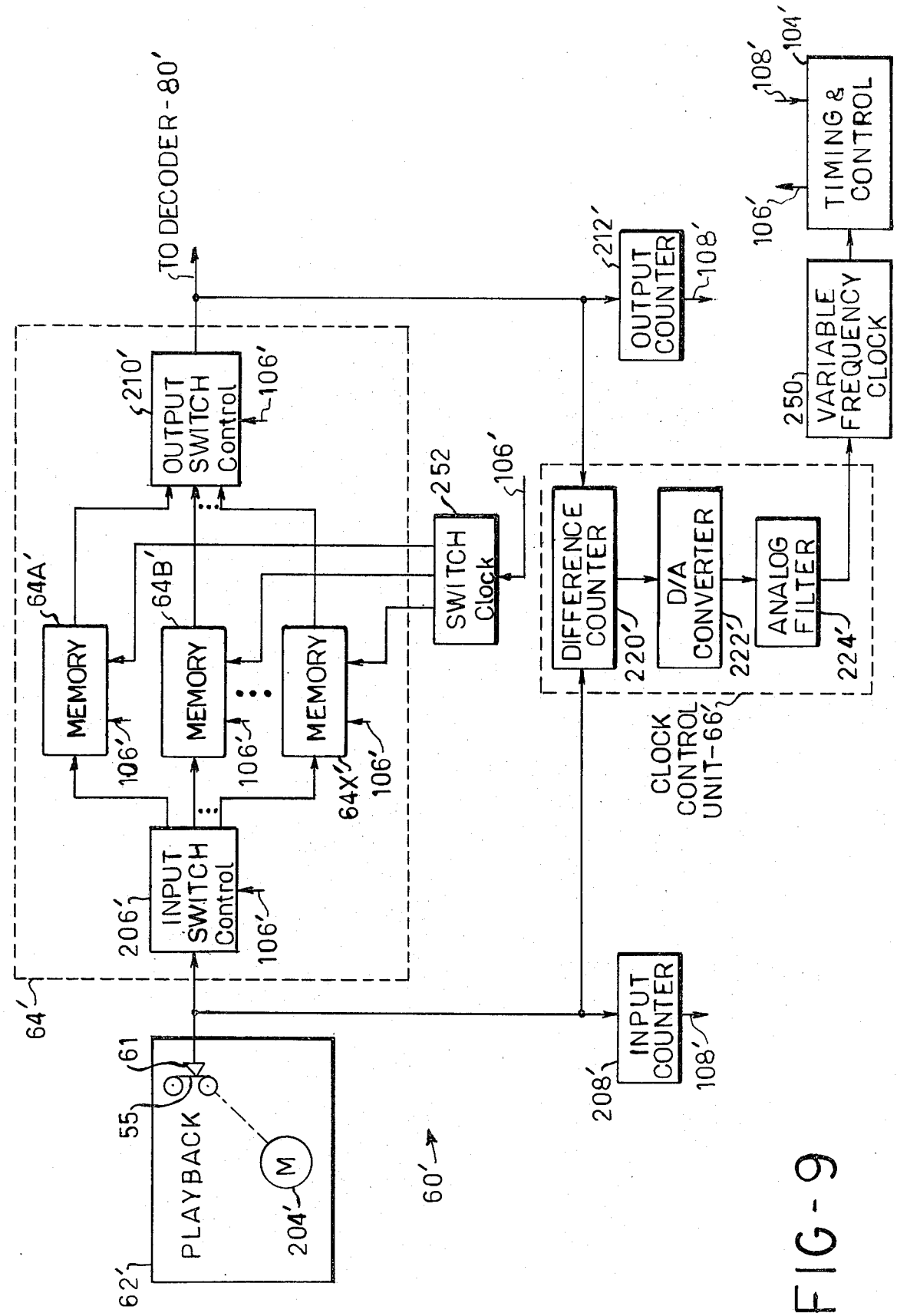
FIG. 9 is a block diagram showing details of the playback unit included in the playback system of FIG. 8.

The constant speed playback unit 60' is shown in FIG. 9 to which figure reference now is made. There, a constant speed motor 204' in the tape transport mechanism drives the recorded tape 55 at a constant rate relative to the pick-up head 61. Elements of the buffer memory means 64' are the same as those included in buffer memory means 64 shown in FIG. 6. These include input and output switches 206' and 210', respectively, and memory units 64A', 64B' . . . and 64X'. Since signals are recorded with a substantially constant bit density on the tape 55, and the tape is moved at a constant rate during playback, bits are supplied to the buffer memory 64' from the pick-up head 61 at a substantially constant bit rate.

As noted above, the read out rate from the buffer memory means is dependent upon the difference in the number of bits written into the buffer memory and the number read out therefrom. As with the playback system shown in FIG. 5, a difference counter 220' having inputs from both the input to and the output from the buffer memory means 64' is provided, which counter has an output which is directly related to the difference in the counts of the two inputs. A digital to analog converter 222' converts the difference signal to analog form, and a low pass filter 224 filters the output from the D/A converter.

The analog control signal from the filter 224' of the clock control unit 66' is supplied to a variable frequency clock 250 for control of the clock frequency, with the clock frequency increasing and decreasing with an increase and decrease, respectively, in the difference in the number of bits written into the buffer memory 64' and the number read out therefrom. The variable frequency clock output is connected to the timing and control unit 104' for control of timing signals produced thereby. A variable frequency clock signal from the timing and control unit 104' is supplied to the chip enable input of one of the memory units 64A', 64B' . . . 64X' through a switch 252, which switch is operated in synchronism with the output switch 210' for connection of an output from a selected memory unit to the decoder 80'. It will be understood, then, that bits are written into said buffer memory means 64' at a substantially constant bit rate from the pick-up head 61, and are read out therefrom to the decoder 80' at a variable rate directly related to the difference in the number of bits written into the buffer memory means and the number read out therefrom. Variable frequency timing signals from the timing and control unit 104' are supplied to the succeeding circuit means, i.e. to the decoder 80', buffer memory 84', digital reconstruction filter 90' and digital to analog converter 96' for processing the encoded difference signal $H(\Delta_n)$ at the variable rate at which they are read out from the buffer memory unit 84'.

With the modified playback system shown in FIGS. 8 and 9, it will be apparent that reconstructed sample signals from the digital reconstruction filter 90' are produced at a varying word rate, whereas the original sample signals from the A/D converter 20 (or 20') in the recording system are produced at a constant word rate. Consequently, the pitch of the analog signal output from the D/A converter 96' will vary from that of the original signal. A buffer memory unit 64' having a largest practical size is employed in this playback system to minimize the variations in read out rate therefrom, thereby minimizing pitch changes. For consumer and small commercial use, it is not presently practical to employ a buffer memory unit 64' of sufficient size such that no variations in the read out rate therefrom would be required to prevent emptying or overflow during playback. For playback of music, voice, etc, the change in pitch from that of the original signal may be limited to, say, 1 to 2 percent, with the use of existing buffer memory means of reasonable size.

Figure 10:
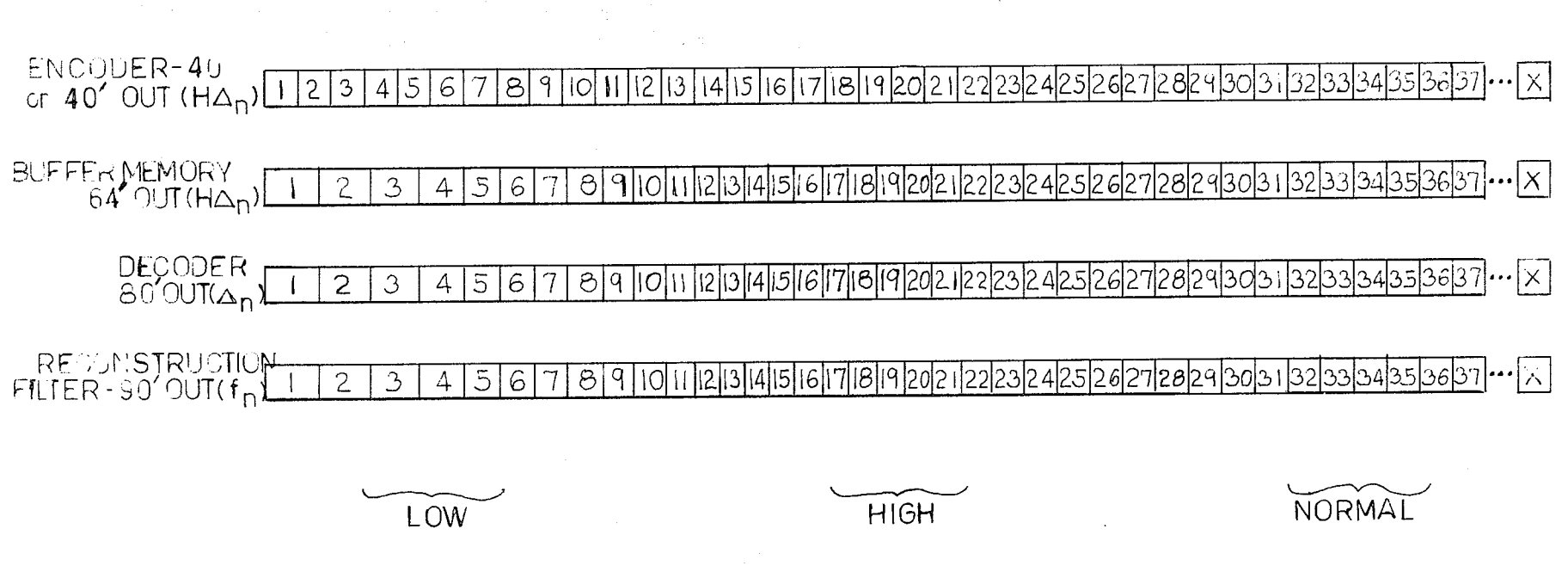

Reference now is made to FIG. 10, wherein different length encoded difference signals $H(\Delta_n)$ are shown to be produced at a substantially constant word rate from the encoder 40 (or encoder 40'), the words being numbered 1, 2, 3 . . . X. The encoded difference signals are recorded on the recording medium 55 (FIG. 3) with substantially uniform bit density using the recording systems shown in FIG. 1A and in FIG. 7. With the modified playback system shown in FIG. 8, the rate at which the encoded difference signals $H(\Delta_n)$ are read out from buffer memory means 64' varies in accordance with the difference in the number of bits written into the buffer memory and the number read out therefrom. In FIG. 10, readout rates for the encoded difference signals are shown to vary from low, to high, to normal. Succeeding stages of the playback system, including the decoder 80' and the reconstruction filter 90' operate at substantially the same word rate, as shown in FIG. 10; different portions of the signal train being labelled low, high, and normal to identify word rates below, above, and at, respectively, the word processing rate of the compression filter and encoder in the associated recording system. It will be apparent, then, that the modified playback system shown in FIG. 8 may be used in situations wherein small variations in word rate from the system are tolerable.

The invention having been described in detail in accordance with requirements of the Patent Statutes, various other changes and modifications will suggest themselves to those skilled in this art. For example, the system is not limited to the illustrated single channel arrangement shown herein and described above. If desired, a plurality of signals may be processed and recorded on a single recording track by use of multiplexing and demultiplexing means in the respective recording and playback units. For example, in such a system the recording unit may include a plurality of channels each of which includes an analog to digital converter (such as A/D converter 20) for converting the associated analog input signals to digital form. Each channel is provided with a digital compression filter (such as filter 30) responsive to the output from the associated analog to digital converter for generating difference signals related to the difference between an input thereto and an estimated value thereof. A multiplexer sequentially switches the difference signals from said digital compression filters to a digital encoder (such as encoder 40) for sequentially encoding the difference signals from the compression filter. The serial stream from the digital encoder is recorded by variable speed recording means (such as recorder 50) for recording with a substantially uniform bit density. For playback of the recorded signal a variable speed playback unit (such as unit 60) may be employed, together with a decoder (such as decoder 84). A demultiplexer separates the decoded serial stream from the decoder into separate signal channels, each of which channels includes a digital decompression filter (such as filter 90) for converting the difference signals to fixed length signals. Digital to analog converters (such as converter 98) may be included in each channel to convert the signals to analog form.

Obviously, the recording and playback means may make use of a recording medium other than tape shown herein; numerous other recording media being known in the art, including non-magnetic recording media.

It also will be understood that the present invention may be used for recording and playback of a variable rate bit stream from any source. That is, the recording and playback units may be used in systems which do not necessarily include the illustrated compression-decompression filter combination, encoder-decoder combination, and/or A/D-D/A converter combination. They may be used, for example, for recording and playback of fixed length words in which the words are produced at a varying rate. However by using the illustrated arrangement, a maximum amount of analog information may be stored on a minimum amount of recording medium.

It is intended that the above and other such changes and modifications shall fall within the spirit and scope of the invention as defined in the appended claims.

We claim:

1. In a digital recording system for recording a bit stream in which bits occur at a varying bit rate on a recording medium with a high and substantially constant bit density, the combination comprising
   buffer memory means for temporarily storing said bits to be recorded,
   variable speed recording means for recording bits from said buffer means on a recording medium, and
   means responsive to the number of bits contained in said buffer memory means for continuously controlling both the rate at which bits are read from said buffer memory means to said recording means and the speed of said recording means for recording said varying bit rate stream with a substantially constant high bit density on said recording medium.

2. In a digital recording system as defined in claim 1 wherein the bit stream to be recorded comprises a stream of variable length words occurring at a substantially constant word rate.

3. In a digital recording system
   for recording on a recording medium a bit stream in which bits occur at a varying bit rate, the combination comprising
   buffer memory means for temporarily storing said bits to be recorded,
   variable speed recording means for recording bits from said buffer memory means on a recording medium, and
   means for continuously controlling both the rate at which bits are read from said buffer memory means to said recording means and the speed of said recording means for recording said bit stream with a substantially constant bit density on said recording medium,
   said controlling means including means for counting the difference in the number of bits of the bit stream written into said buffer memory means and the number of bits read out of said buffer memory means to said variable speed recording means.

4. In a digital recording system as defined in claim 3 wherein the rate at which bits are read from said buffer memory means and the speed of said recording means are in direct proportion to the output from said counting means.

5. In a digital recording system for recording a bit stream having a varying bit rate on a recording medium with a substantially constant bit density, the combination comprising
   buffer memory means into which said varying bit rate stream to be recorded is written for temporary storage of said bits,
   variable speed recording means for recording bits from said buffer memory means on a recording medium, and
   means for controlling both the rate at which bits are read from said buffer memory means to said variable recording means and the speed of said variable speed recording means in direct proportion to the difference in the number of bits written into said buffer memory means and the number read out therefrom.

6. In a digital recording system for recording a bit stream having a varying bit rate on a recording medium with a substantially constant bit density, the combination comprising
   buffer memory means into which said varying bit rate stream to be recorded is written for temporary storage of said bits,
   variable speed recording means for recording bits from said buffer memory means on a recording medium, said variable speed recording means including a recording head and a variable speed motor for relatively moving said recording head and recording medium, and
   means for controlling both the rate at which bits are read from said buffer memory means to said variable recording means and the speed of said variable speed recording means in direct proportion to the difference in the number of bits written into said buffer memory means and the number read out therefrom, said controlling means including
   means responsive to the difference in the number of bits written into said buffer memory means and the number read out therefrom for obtaining a control signal proportional to said difference.
   a variable frequency clock,
   means for connecting said control signal to said variable frequency clock for controlling the clock frequency,
   means for connecting the output from said variable frequency clock to said buffer memory means for establishing the rate at which bits are read from said buffer memory means, and
   means for connecting said control signal to said variable speed motor for control of the motor speed.

7. In a digital recording system as defined in claim 6 wherein the recording medium comprises recording tape movable by said variable speed motor past said recording head.

8. In a digital recording system as defined in claim 5 wherein the bit stream to be recorded comprises a stream of variable length words produced at a substantially constant word rate.

9. In a recording system for compactly recording digital data on a recording medium, the combination comprising a source of fixed word length digital signals, digital compression filter means for digital compression of said digital signals from said source, digital encoding means for encoding the output from said digital compression filter means, the output from said encoding means comprising variable word length signals, buffer memory means for temporary storage of the variable word length signals from said encoding means, variable speed recording means for recording the variable word length signals read out from said buffer memory means, and means for controlling both the rate at which bits are read out from said buffer memory means to said recording means and the recording speed of said recording means in direct proportion to the number of bits written in said buffer memory means and not yet read out therefrom.

10. In a recording system as defined in claim 9 wherein the ratio of the read out rate from said buffer memory means and the recording speed provides for recording on the recording medium with substantially maximum bit density.

11. In a recording system as defined in claim 9 wherein said source of fixed word length digital signals comprises analog to digital converter means for converting an analog input signal into fixed word length digital signals.

12. In a method of recording a bit stream in which the bits occur at a varying bit rate, the steps including transferring the varying bit rate stream to be recorded to continuously variable speed recording means through buffer memory means for recording of the bit stream on a recording medium included in said variable speed recording means, and continuously controlling the read out rate of bits from said buffer memory means and the speed of operation of said variable speed recording means as a function of the number of bits contained in said buffer memory means for recording of the varying bit rate stream with substantially constant bit density on the recording medium.

13. In a method of recording as defined in claim 12 wherein the step of controlling the read out rate of bits from said buffer memory means and the speed of operation of said variable speed recording means is in response to the difference in the number of bits written into said buffer memory means and the number read out therefrom.

14. In a method of digital recording a varying bit rate stream of bits such as a stream of variable length words produced at a substantially constant word rate, or the like, on a recording medium with substantially constant bit density, the steps including feeding said stream to buffer memory means for temporary storage of the stream bits, reading bits from said buffer memory means to variable speed recording means for recording the same, controlling the rate at which bits are read out from said buffer memory means and the recording speed of said variable speed recording means in direct proportion to the difference in the number of bits written into said buffer memory means and the number of bits read out therefrom to record said bits with a substantially constant bit density.

15. In a playback system for playback from a recording medium upon which variable word length digital signals are recorded with a substantially uniform bit density, the combination including circuit means for processing variable word length digital signals at a substantially constant word rate, variable speed playback means, including a pickup head and a variable speed motor for relatively moving said pickup head and recording medium, for playing back recorded variable word length digital signals from said recording medium, buffer memory means into which variable word length digital signals from said variable speed playback means are written for temporary storage thereof and from which said stored signals are read out to said circuit means, and means responsive to the difference in the number of bits written into said buffer memory means and the number read out therefrom for controlling the motor speed of said variable speed playback means in inverse proportion to the output from said difference responsive means for constantly maintaining a supply of digital signals in said buffer means for use by said circuit means.

16. In a playback system for reproducing original fixed word length digital signals which have been compressed and encoded using variable length code words and recorded with a substantially uniform bit density on a recording medium, the combination comprising, variable speed playback means for playing back the recorded encoded signals from said recording medium, buffer memory means into which encoded signals from said playback means are written for temporary storage thereof, decoder means operable at a substantially constant word rate, means for reading out encoded signals from said buffer memory means to said decoder means for decoding said signals, digital decompression filter means responsive to the decoded output signals from said decoder means for digital reconstruction of the original fixed word length digital signals, and means for controlling the speed of operation of said variable speed playback means to maintain the buffer memory means partially full.

17. In a playback system as defined in claim 16 wherein said controlling means includes means for producing a control signal in response to the difference in the number of bits written into said buffer memory means and the number read out therefrom.

18. In a playback system for playback of digital signals from a recording medium upon which digital signals comprising variable length words are recorded with a substantially uniform bit density, the combination including, uniform speed playback means for playing back recorded digital signals from said recording means, buffer memory means into which variable word length digital signals from said uniform speed playback means are written at a substantially constant bit rate for temporary storage thereof and from which said stored signals are read out at a varying bit rate, circuit means operable at a varying word rate for processing variable word length digital signals read out from said buffer memory means, and means for simultaneously controlling both the rate at which bits are read out from said buffer memory means and the word rate at which said circuit means operates to prevent overflow or emptying of said buffer memory means during playback.

19. In a playback system as defined in claim 18 wherein
the read out rate from said buffer memory means and word rate of operation of said circuit means deviates no more than substantially 1% from a fixed word rate.

20. In a playback system for playback of digital signals from a recording medium upon which digital signals are recorded with a substantially uniform bit density, the combination including,
uniform speed playback means for playing back recorded digital signals from said recording means,
buffer memory means into which digital signals from said uniform speed playback means are written at a substantially constant bit rate for temporary storage thereof and from which said stored signals are read out at a varying bit rate,
circuit means operable at a varying word rate for processing digital signals read out from said buffer memory means, and
means for controlling the rate at which bits are read out from said buffer memory means and the word rate at which said circuit means operates to prevent overflow or emptying of said buffer memory means during playback,
said controlling means including means responsive to the difference in the number of bits written into said buffer memory means and the number read out therefrom for controlling the rate at which bits are read out from said buffer memory means and the rate of operation of said circuit means in direct proportion to the output from said difference responsive means.

21. In a playback system for reproducing original fixed word length digital signals which have been compressed and encoded using variable length code words and recorded with a substantially uniform bit density on a recording medium, the combination comprising,
uniform speed playback means for playing back the recorded encoded signals from said recording medium,
buffer memory means into which encoded signals from said playback means are written for temporary storage thereof,
decoder means operable at a variable word rate,
means for reading out encoded signals from said buffer memory means to said decoder means for decoding said signals,
digital decompression filter means operable at a variable word rate and responsive to the decoded output signals from said decoder means for digital reconstruction of the original fixed word length digital signals, and
means for controlling the read-out rate from said buffer memory means and rate of operation of said decoder means and digital decompression filter means to prevent overflow of said buffer memory means and emptying thereof during playback from the recording medium.

22. In a playback system as defined claim 21 wherein said controlling means includes means for producing a control signal in response to the difference in the number of bits written into said buffer memory means and the number read out therefrom.

23. In a playback system as defined in claim 21 wherein the word rate of operation of said decoder means and digital decompression filter means is within substantially ±1 percent of a fixed word rate.

24. A system for recording analog signals, such as music, or the like, in compact digital form on a recording medium, comprising in combination
means for converting said analog signals to be recorded to fixed word length digital signals,
digital compression filter means for digital compression of said digital signals from said converting means,
digital encoding means for encoding the output from said digital compression filter means, the output from said encoding means comprising variable word length signals,
buffer memory means for temporary storage of the variable word length signals from said encoding means,
uniform speed recording means for recording the variable word length signals read out from said buffer memory means, and
means for reading bits out of said buffer memory means at a substantially uniform bit rate of recording thereof with a substantially constant bit density on the recording medium.

* * * * *